(12) United States Patent
Shao et al.

(10) Patent No.: US 8,481,266 B2
(45) Date of Patent: Jul. 9, 2013

(54) DNA SEQUENCING METHOD AND SYSTEM

(75) Inventors: Zhifeng Shao, Shengzhen (CN); Sitong Sheng, Shenzhen (CN)

(73) Assignee: Hyk Gene Technology Co., Ltd., Shenzhen (CN)

( * ) Notice: Subject to any disclaimer, the term of this patent is extended or adjusted under 35 U.S.C. 154(b) by 166 days.

(21) Appl. No.: 12/742,995

(22) PCT Filed: Nov. 17, 2008

(86) PCT No.: PCT/CN2008/073092
§ 371 (c)(1),
(2), (4) Date: May 14, 2010

(87) PCT Pub. No.: WO2009/065355
PCT Pub. Date: May 28, 2009

(65) Prior Publication Data
US 2011/0045992 A1    Feb. 24, 2011

(30) Foreign Application Priority Data
Nov. 16, 2007  (CN) .......................... 2007 1 0170507

(51) Int. Cl.
*C12Q 1/68*        (2006.01)
*C12P 19/34*       (2006.01)

(52) U.S. Cl.
USPC ........................ 435/6.12; 435/6.1; 435/6.11

(58) Field of Classification Search
None
See application file for complete search history.

(56) References Cited

U.S. PATENT DOCUMENTS

2008/0242560 A1*  10/2008  Gunderson et al. ............. 506/26

\* cited by examiner

*Primary Examiner* — Young J Kim
(74) *Attorney, Agent, or Firm* — Rosenberg, Klein & Lee

(57) ABSTRACT

The present invention relates to the field of gene engineering, provides a DNA sequencing method and system. Said DNA sequencing method includes following steps: A. said DNA is processed into multiple DNA segments, and then constructed into multiple DNA tags; B. amplification of every single DNA tag, and then processed into single stranded DNA; C. Utilize the anchor which can ligate to DNA tags and possesses at least one degenerated base to sequence every single DNA tag and thus produce sequencing signal; D. Obtain sequences of every single DNA segment by sequencing signal. Said DNA sequencing system, includes: unit of short tags construction, unit of amplification, unit of sequencing reaction and unit of signal processing. In this invention, since DNA tags are sequenced by using sequencing anchor with at least one degenerative abase, length of DNA tags that can be directly sequenced is extended. Both short and long DNA tags can be sequenced. Thus application of DNA sequencing is expanded.

22 Claims, 9 Drawing Sheets

DNA SEQUENCING METHOD AND SYSTEM

FIELD OF THE INVENTION

The present invention relates to the field of gene engineering, and more particularly to DNA sequencing method and system.

BACKGROUND OF THE INVENTION

With increasing number of completely sequenced genomes, more and more information needs to be analyzed, such as enormous encoding messages of these genome sequences, controlling elements of different genes dispersed in genomes, and their biological function involved. Sequence analysis methods developed from functional genome research mainly includes microarrays and quantitative assay based on isolated DNA sequence.

Most used microarray platforms are oligonucleotide arrays. In this technology, different oligos representing different segments of the genome are immobilized on a vector's surface, and then the array is hybridized with samples proportionally. Thus the strength of hybridization signal defines target sequence relative abundance. The major advantage of oligonucleotide arrays is the convenience to handle, and the ability of its massively parallel operation. However, global analysis of gene expression profile in tissue or cells is difficult to be obtained with microarray technology. In addition, microarray technology needs to predetermine gene probes to be synthesized. Thus some unknown and less abundant expressed genes could be missed in the assay. Furthermore, cross hybridization phenomena may influence the accuracy of the results.

Currently the most commonly used method is quantitative assay based on isolated DNA sequence. In this type of method, originally used method is SAGE (Serial analysis of gene expression). This method is to analyze expression status of groups of genes in certain tissue or cell types based on sequencing technology. The prevailing method is a polony sequencing method used in Church's group. This technology is a revised version of SAGE. Its sequencing process is illustrated in FIG. 1, including the following steps: Step 11, processing DNA template into DNA tag by random sonication or molecular biology method; Step 12, DNA tag is immobilized on microbeads by amplification through emulsion PCR (Polymerase Chain Reaction), and these microbeads are then embedded in agarose and tightly arrayed on glass surface. Step 13, parallel sequencing of DNA tags on microbeads via Ligation. First, hybridize between single strand DNA and sequence anchor, and then ligase select base through the ligation of 4 fluorescent labeled oligonucleotide. This process will produce sequencing signal. In this step, since sequencing anchor used is immobilized anchor, bases that can be called is less than 7 by ligation reaction. Step 14, sequencing signal are collected, images are processed and bases are called. Correctly ligated base can be imaged by fluorescence label.

In the above said technology, bases to be sequenced by sequencing anchor are generally within 7 bases from sequencing anchor. Only short DNA tags can be sequenced. Since sequences obtained are relatively too short, it is hard to map obtained sequence back into genome sequences. Thus sequencing information is difficult to be used efficiently. Furthermore, the immobilization of micro-beads is through embedding beads in gel on surface of slides. In this way, density of micro-beads can't be very high. Throughput and reaction efficiency are difficult to improve. In addition, when 4 color fluorescence labeling system is adapted, signal strength difference among different fluorescence could affect the result. Different signal can even be masked by background. Therefore sequencing results could be inaccurate or misleading.

Thus a new sequencing method is needed to enlarge the application area of DNA sequencing. This new method should be higher throughput, reaction efficiency and accuracy.

BRIEF SUMMARY OF THE INVENTION

One of the aims of this invention is to provide a sequencing method, thus to expand the applicable range of DNA sequencing technology.

To embody this invention aim, said DNA sequencing method include following steps:
A. Said DNA is processed into multiple DNA segments, and then constructed into multiple DNA tags;
B. Amplification of every single DNA tag, and then processed into single stranded DNA;
C. Utilizing a sequencing anchor which is operable to hybridize to the DNA tags and contains at least one degenerate base to sequence every single DNA tag and thus produce sequencing signal; and
D. Obtaining sequences of every single DNA tag by sequencing signal.

Step A includes:
A1: Ligating a first adaptor sequence to both ends of the DNA fragments;
A2: Cutting the ligated product with a restriction enzyme to generate a free 3' end and a free 5' end for each of the DNA fragments;
A3: Ligating a second adaptor sequence to the free 3' and 5' ends to produce DNA tags of equal size, the DNA tags each including the first adaptor sequence; said first adaptor sequence including a sequence complementary to a sequencing anchor, sequences of amplification primers, and Type II restriction enzyme site used to process the DNA fragments into DNA tags of equal size; said amplification primers being configured for PCR; and said second adaptor sequence further including an anchor sequence for normalization of sequence signals.

Prior to said step A1, the method to process DNA into multiple DNA fragments includes: Fragmenting the DNA physically or cleaving the DNA by DNA enzyme.

In another aspect, in said step B amplification can be PCR.
Said step B includes:
B1. Immobilize PCR primers included in first adaptor sequence of DNA tags on vector's surface.
B2. Compartmentalizing the product of step B1 into independent reactors, wherein each reactor includes an independent DNA tag.
B3. Generating PCT in the said reactors and produce multiple copies of DNA tag.
B4. Processing the obtained DNA tags into single stranded DNA.

As used herein, the said B1 step includes immobilization of PCR primers on vector's surface through 5' covalently bond or biotin binding.

As used herein, the said vector in Step B1 includes glass slide or microbeads.

As used herein, reactors can be picoliter reactors.

As used herein, when the said vector is glass slide, then the said Step B2 includes: putting a cover made from soft silicon material and having picoliter volume holes over a glass slide, and thereby each picoliter volume hole is a picoliter volume reactor.

As used herein, the said vector is micro-beads, then the said Step B2 includes: dispersing micro-beads into oil and forming the suspend picoliter reactor droplets. Each picoliter reactor droplet is an independent picoliter reactor.

As used herein, the said vector is micro-beads, then the said Step B2 includes: dispersing micro-beads into PCR system, and then dispersing the PCR system into oil and forming the suspend picoliter reactor droplets. Each picoliter reactor droplet is an independent picoliter reactors.

As used herein, after the said Step B3 is a process which involves in enrichment of micro-beads, including:

Immobilizing micro-beads on a level surface by amino covalently linked and forming an enriched array.

As used herein, the said Step C includes:

C1: Hybridization between sequencing anchor containing K number of degenerate bases and DNA tag immobilized on vector surface. As used herein, K is a positive integer.

C2: Extension along DNA tag by the K number of degenerate bases in the sequencing anchor, to produce the sequence signal along the process.

Before said step C includes step C': artificially synthesizing said sequencing anchor.

Said Step C2 includes following step: C2': Utilizing the anchor sequence for normalization of the sequence signal in ligation reaction to promote normalization signal.

Said step C2 further includes an overlapping sequencing mechanism, after the extension of DNA tag by the K number of degenerate bases in the sequencing anchor to produce the sequence signal along the process, the sequencing anchor is replaced with normalization anchor, which is complementary to the anchor sequence for normalization of sequence signal in second adaptor sequence, to repeat said extension step, then the sequence of every single DNA tag is bi-directionally sequenced from both ends of the DNA tag.

Said step C2 includes Type IIs restriction enzyme walking mechanism, i.e. utilizing Type IIs restriction enzyme site in adaptor sequence of DNA tags, cutting off portion of DNA that has been sequenced, and then adding on new adaptor sequence to the Type II restriction enzyme site and forming new and shortened DNA tags, and further sequencing from new adaptors, and finally obtaining sequence results of the remaining regions in DNA tags.

Said sequencing anchor with K number of degenerate bases includes extension primer or PCR extension primer.

When said sequencing anchor with K number of degenerate bases is extension primer, step C2 includes ligation reaction between said extension primer and degenerate polymers with fluorescent end label, and then extension along DNA tag, and producing sequencing signal along the extension.

Said degenerate polymers are respectively labeled by two or four kinds of fluorescent labels with different colors.

When said sequencing anchor with K number of degenerate bases is PCR extension primer, step C2 includes adding in DNA polymerase, nucleotide, labeled (biotin-labeled or fluorescence-labeled) nucleotide, extending along 3' end of DNA tag by polymerase, and producing sequencing signal along extension process.

When said sequencing anchor with K number of degenerate bases is PCR extension primer, step C2 further includes after step C2, removing DNA extended by polymerase along extension primer from the DNA tag immobilized on the vector's surface.

As used herein, said removing DNA extended by polymerase along extension primer includes: denature, or exonuclease digestion, or denature accompanied by digestion.

Said step D includes:

D1: Collecting sequencing signal by optical imaging;

D2: Calling different bases corresponding to different signal, i.e. said sequence of DNA fragment.

Said step D1 includes, collecting simultaneously sequencing signal and normalization signal by optical imaging.

To better embody the aim of this invention, a DNA sequencing system is also provided, including:

Unit of short tags construction, aiming to process DNA into multiple DNA fragments and further construct into multiple DNA tags;

Unit of amplification, connected to unit of short tags construction, aiming to amplify every single DNA tags;

Unit of sequencing reaction, connected to unit of amplification, aiming to utilize anchor which is operable to hybridize to the DNA tags and contains at least one degenerate base, sequence every single DNA tag and produce sequencing signal.

Unit of signal processing, connected to unit of sequencing reaction, aiming to obtain sequences of every single DNA fragment from sequencing signal.

Said sequencing reaction, includes:

Reaction chamber. Vector is placed on one of its inner wall. Multiple DNA tags are immobilized on said vector's surface. Receiving sequencing reaction reagents, sequencing of said DNA tags can be conducted in reaction chamber, and producing sequencing signal.

Reagent entry and exit are separately placed at the ends of the other side of the inner reaction chamber wall. Both are provided channels separately for reaction reagent entering and for reaction reagent exiting.

Said unit of signal processing includes:

Data collecting module, used for collecting sequencing signal;

Data processing module, used for calling sequences of every single DNA fragment based on sequencing signal.

From the last known, since during the DNA sequencing process, this invention utilize sequencing anchor with at least one degenerate base, length of DNA tags that can be directly sequenced is extended and application range of DNA sequencing is also expanded.

These and other advantages, aspects and novel features of the present invention, as well as details of illustrative aspects thereof, will be more fully understand from the following description and drawing.

To illustrate the aim, technology program and advantages better, this invention will be further described in details, using supplementary figures and exemplary embodiments.

DETAILED DESCRIPTION OF THE INVENTION

In this invention, DNA tags are first constructed based on DNA and forms DNA tags. Then said every single DNA tag is amplified by single molecule amplification. Sequencing of DNA tags is conducted by using sequencing anchor with at least one degenerate base. Sequencing signal is produced along the sequencing process. Then sequencing signal is collected and processed to call sequences of DNA tag. In this invention, since DNA tags are sequenced by using sequencing anchor with at least one degenerate base, length of DNA tags that can be directly sequenced is extended. Both short and long DNA tags can be sequenced. Thus application of DNA sequencing is expanded.

Figure 1:
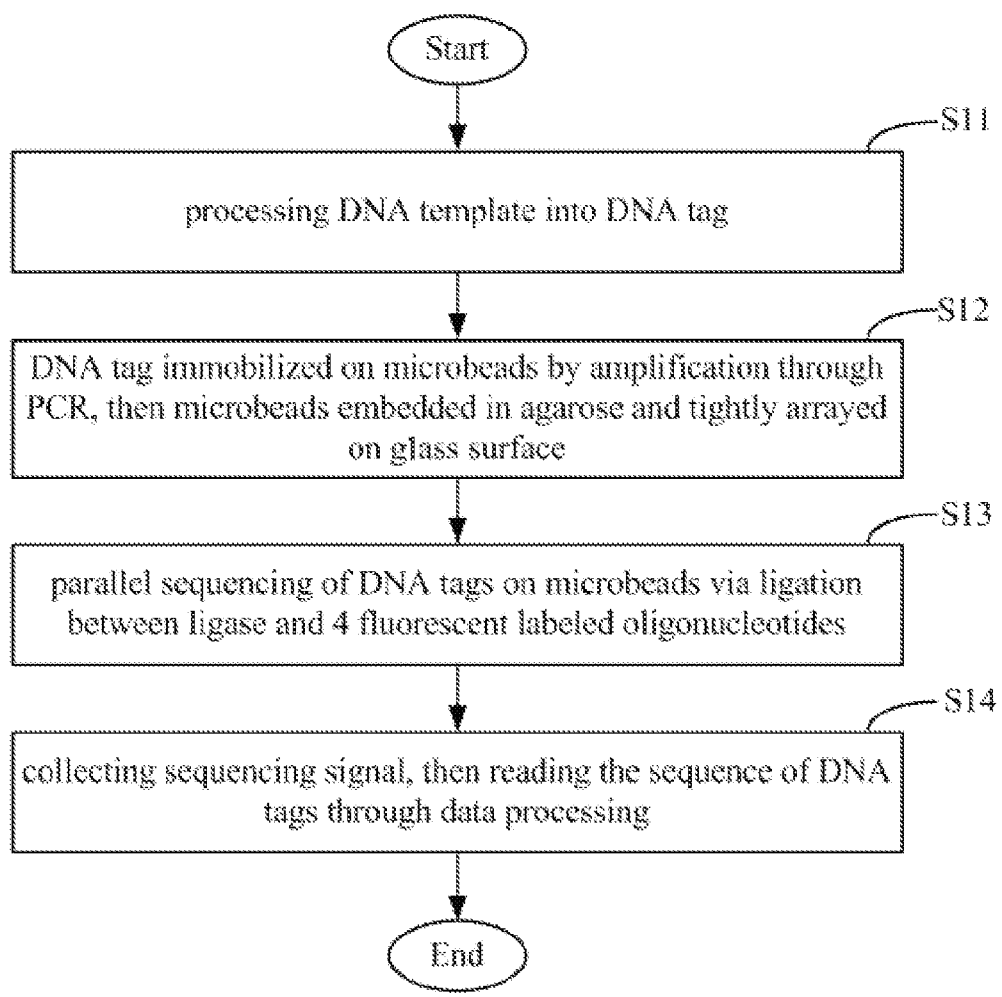
FIG. 1 is a flow chart illustrating sequencing method using current MPSS technology.
Figure 2:
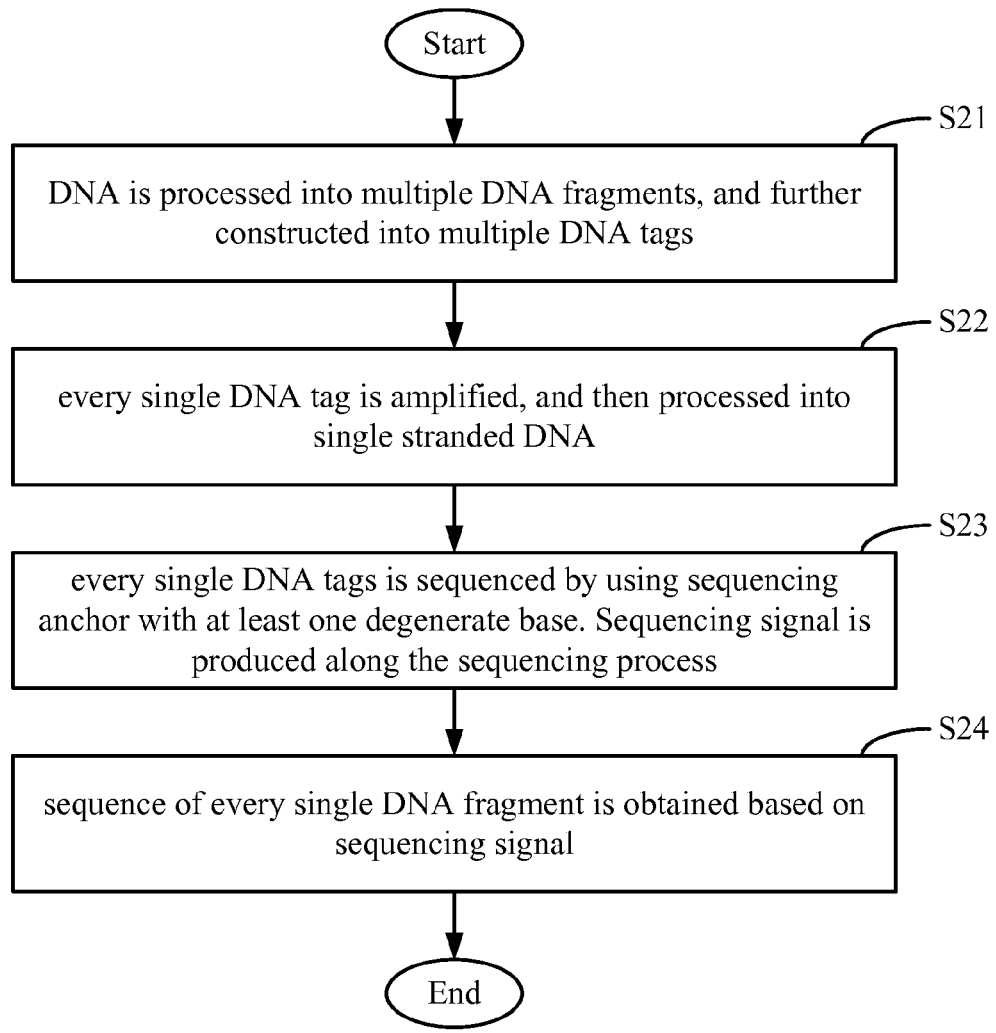
FIG. 2 is a flow chart showing sequencing method used in an exemplary embodiment of this invention.

FIG. 2 shows a process of DNA sequencing method used in an exemplary embodiment of this invention, the details are in the following:

Step 21, DNA is processed into multiple DNA fragments, and further constructed into multiple DNA tags. Details of embodiment of this step will be shown in FIG. 3 and FIG. 4.

Step 22, every single DNA tag is amplified, and then processed into single stranded DNA. Details of embodiment of this step will be shown in FIG. 5.

Step 23, every single DNA tag is sequenced by using sequencing anchor with at least one degenerate base. Sequencing signal is produced along the sequencing process. Details of embodiment of this step will be shown in FIGS. 6, 7, 8 and 9.

Step 24, sequence of every single DNA fragment is obtained based on sequencing signal. Details of embodiment of this step will be shown in FIG. 10.

Figure 3:
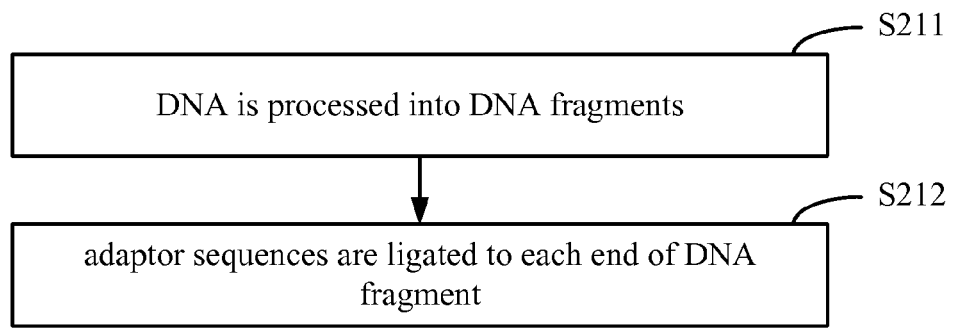
FIG. 3 is a flow chart showing method of DNA tags construction based on DNA used in an exemplary embodiment of this invention.

In one exemplary embodiment, Step 21 in FIG. 2, details of DNA tags construction based on DNA are shown in FIG. 3, including following steps.

Step 211, DNA is processed into DNA fragments. In this invention, methods of processing DNA into DNA fragment can vary, such as fragmenting the DNA physically, or cleaving the DNA by DNA enzyme. Generally, for long DNA fragment, length of DNA can be shortened within the range of hundreds of base pairs by random cut. However, for some application, for example, mRNA expression profile, certain restriction enzyme site is chosen based on requirement and thus converted DNA is cut into DNA fragment with sticky ends Step 212, adaptor sequences are ligated to each end of DNA fragment. Thus DNA tags are constructed. Adaptor sequences include sequences complementary to general sequence in anchor and sequences for amplification primer. In this invention, anchor is used for sequencing of DNA fragment. It is designed according to adaptor sequence. In one optimized embodiment, anchor is called sequencing anchor, including a general sequence and at least one degenerate base. The general sequence is complementary to adaptor sequences in DNA tags. As for sequence anchor, details will be described in FIG. 7, FIG. 9 and exemplary embodiment.

In an optimized exemplary embodiment, constructed DNA tags are collected and forms a tags library. This can be used in the following sequencing reaction and signal collection.

In an optimized exemplary embodiment, besides sequences complementary to general sequence in sequencing anchor, adaptor sequence includes anchor sequence of normalization for sequencing signal, called normalization anchor.

In this invention, there are multiple amplification primers. In an exemplary embodiment, amplification primers are PCR primers.

Figure 4:
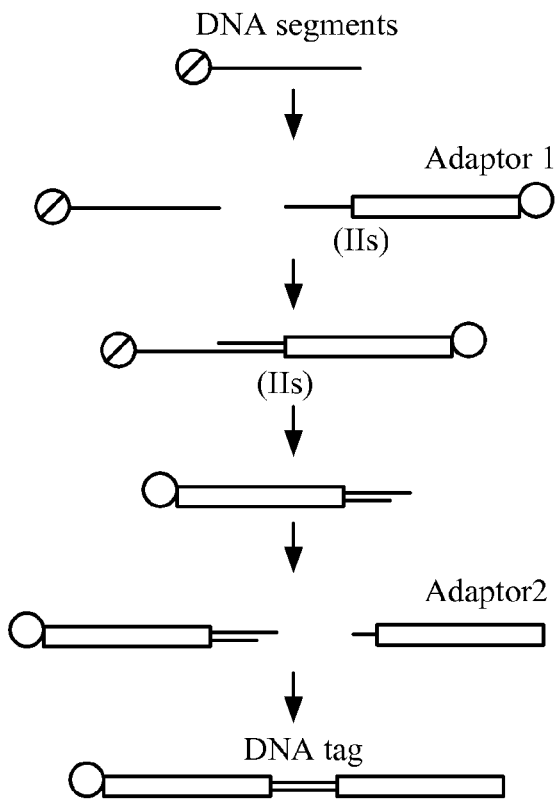
FIG. 4 is a schematic diagram showing DNA tags construction based on DNA used in an exemplary embodiment of this invention.

In an exemplary embodiment, process of DNA tags construction is shown in FIG. 4.

First, DNA is processed into DNA fragment. At this stage, adaptor sequences need to be designed. It needs to be described that for randomly cut DNA fragment, adaptor sequence is designed to have 6 random bases overhanger on its 5' end. This overhanger can be paired with sequences with 6 complementary bases on its 3' ends. As for sticky end DNA fragment, adaptor sequence can be designed to have complementary ends that can be ligated with double stranded DNA. In this exemplary embodiment, in order to produce DNA tags at the same length, the designed first adaptor sequence should have one of type II restriction enzyme sites.

Then DNA fragments are denatured into single stranded DNA. The denatured DNA is ligated with first adaptor sequence. Thus a ligation reaction is completed. Since there is one of Type II restriction enzyme site in the first ligation sequence, through cutting DNA fragment ligated with the first adaptor sequence, a small fragment together with the first adaptor sequence is cut off. Thus ligated DNA fragment can be processed at the same length.

DNA fragments are immobilized with the first adaptor sequence. Their free ends can be repaired to blunt ends and be ligated with the second adaptor sequence. Therefore DNA tags are constructed with two adaptor sequence.

Figure 5:
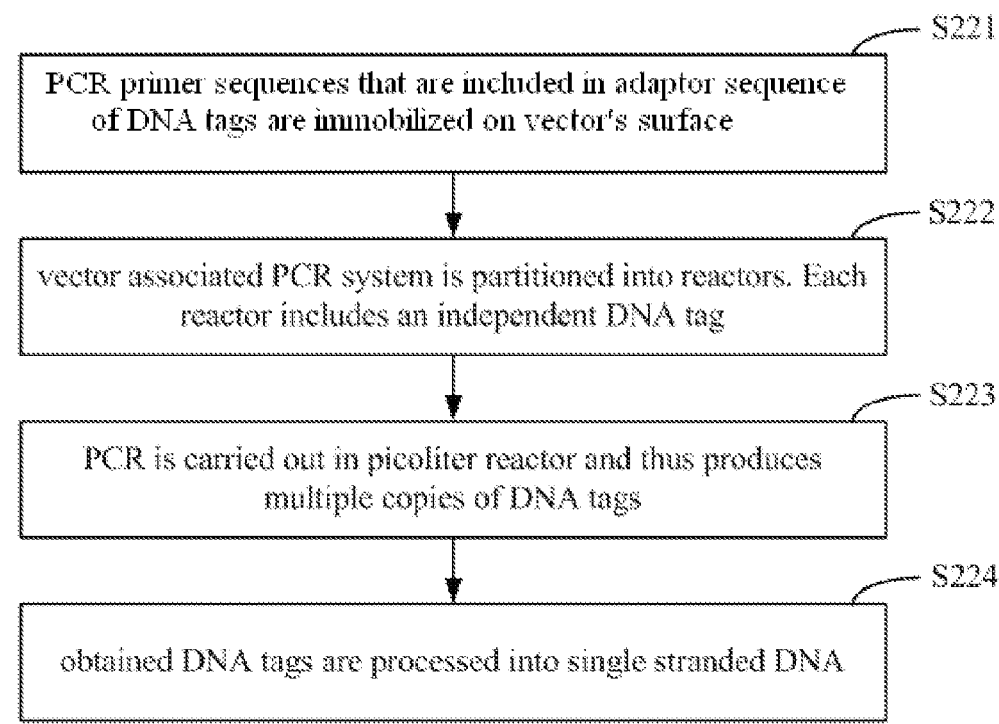
FIG. 5 is a flow chart illustrating method of DNA tags amplification by single molecule PCR used in an exemplary embodiment of this invention.

In an exemplary embodiment, Step 22 in FIG. 2, the detailed process of DNA tags amplification is shown in FIG. 5. There are various ways to amplify DNA tags in this invention. In this exemplary embodiment, single molecule PCR is used to embody amplification. Thus said amplification primers in adaptor sequences of DNA tags are PCR primers Amplification process in detail includes following steps.

In Step 221, PCR primers that are included in adaptor sequence of DNA tags are immobilized on vector's surface. In this invention, said vector can be various forms, such as glass slides, micro-beads and etc. In an optimized exemplary embodiment, this step is to immobilize PCR primers through covalently linked or biotin binding on vector's surface such as glass slide or micro-beads or etc.

In Step 222, vector associated PCR system is partitioned into reactors. Each reactor includes an independent DNA tag. In this invention, said PCR system includes primers, DNA polymerase, DNA tags, dNTP, buffers and etc. In the above steps, said reactors typically are picoliter reactors. However, in this invention, reactors can be the ones besides the described, for example, can be nanoliter reactors and etc. When said Step 221 vectors vary, picoliter reactors in Step 222 can differ.

In an exemplary embodiment of the above step, when vector is glass slide, process of construction of picoliter reactor is as the following: cover made of soft material and with small holes of picoliter volume is overlaid on the surface of glass slides. Thus PCR system is partitioned into picoliter reactors. Said soft material can be PDMS, and can be made as a cover with small holes of picoliter volume.

In another exemplary embodiment of the above step, when vector is micro-beads, process of construction of picoliter reactor is as the following: microbeads are dispersed into PCR system. Then PCR system is placed into oil liquid and forms suspend picoliter drops with micro-beads. Each picoliter reaction droplet is an independent picoliter reactor.

In Step 223, PCR is carried out in picoliter reactor and thus produces multiple copies of DNA tags.

In Step 224, obtained DNA tags are processed into single stranded DNA. In an exemplary embodiment, single stranded DNA tags can be obtained by alkaline denature of DNA tags.

It should be stated that if the vector used in this invention is micro-beads, after Step 223, an enrichment process should be included. The process includes (1) first, DNA tags bound on micro-beads are amino-modified; (2) Then micro-beads are bound to the surface of loading film through amino covalently linked and form an enrichment array. Herein, loading film is transparent material that can be used to load samples, such as glass slides, plastics, quartz and etc. In this invention, micro-beads with DNA tags are bound to special modified glass slide's surface using amino chemistry. This method is very efficient. Fill factor is near 70% of its useful surface. It won't have overlapping problem even with over-loaded micro-beads. More importantly, unbound micro-bound can easily be collected and saved for next experiment and won't lose their function.

In the above process of enrichment of micro-beads, step (1) Methods of amino modification of DNA tags on micro-beads can be multiple kinds:

In an exemplary embodiment, DNA bound on micro-beads can be ligated with amino modified nucleotide. Amino modified nucleotide, for example, aa-dUTP (aminoallyl-dUTP), aa-dCTP (aminoallyl-dCTP) and etc. can be independently or together with dNTP added into TdT (Terminal transferase) reactions, thus labeling DNA molecules. One option is that dideoxynucleotide can be added at appropriate ration to limit the length of the terminals.

In another exemplary embodiment, amino modified oligonucleotide can be dual labeled with psoralen through binding with complementary DNA on micro-beads by laser activation. Thus DNA tags can be amino modified.

In the above process of enrichment of micro-beads, step (2) micro-beads are covalently bound to surface of loading film by amino binding. End of the covalently binding unit can be of amine family or hydroxyl family. This covalent stable immobilization can be the binding of hydrazine with aldehyde or ketone. This covalent binding process can be embodied by covalent binding of one of the several loading film as the following:

In the first exemplary embodiment, loading film (glass or polystyrene) can be amino modified. After adding carbodiimide such as EDC (1-Ethyl-3-(3-dimethyllaminopropyl) carbodiimide) and etc., amino group on loading film can be paired with hydroxyl and forms amino group.

In the second exemplary embodiment, loading film (glass) is silylated by amino modification. Silylated surface includes a silylated film including silane molecules with functional amino group.

In the third exemplary embodiment, loading film (glass) is modified by silylation. However, the silylated film has the following functional groups: aldehyde, epoxy, amber imine or mixture of the above groups. These functional groups can interact with one or other. This interaction can be covalent or non-covalent. This interaction can be carried out on DNA or oligo on micro-beads without modification or with amino modification.

In the fourth exemplary embodiment, loading film (polystyrene) contains amino group after modification. Thus it can bind amino modified oligonucleotide or DNA by covalently linked. This modification can be done on micro-beads. Surface of amino modified polystyrene is done by hydrazine compounds of aromatic family, such as SANH (C6-succinimidyl 6-hydrazinonicotinate acetone hydrazone) or SHTH (succinimidyl 4-hydrazidoterephtalate hydrochloride). DNA or oligonucleotide is modified through aldehyde group. SFB (C6-succinimidyl 4-formylbenzoatecan be modified by this aldehyde compound. When the above compound mixed together, hydrazine group interact with aldehyde and transforms into hydrazone compound.

It should be stated that, this invention is not limited by the above exemplary embodiments. Other similar processing method should be protected by this invention.

Figure 6:
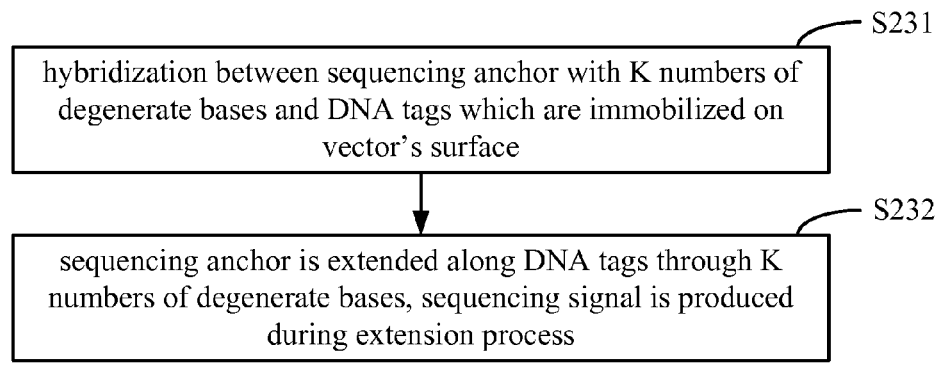
FIG. 6 is a flow chart illustrating DNA sequencing method utilizing sequencing anchor with at least one degenerate base used in an exemplary embodiment of this invention.
Figure 7:
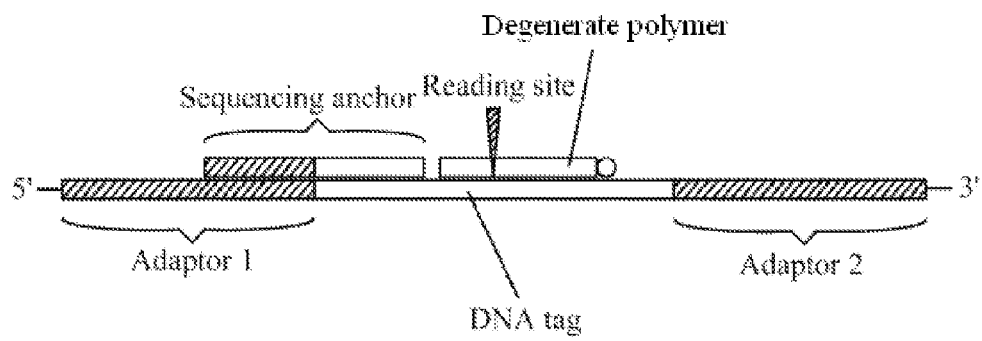
FIG. 7 is a schematic diagram showing sequence process using extended primer as sequencing anchor as used in an exemplary embodiment of this invention.

In an exemplary embodiment, Step 23 in FIG. 2, detailed process of sequencing of DNA tags by using sequencing anchor with at least one degenerate base is shown in FIG. 6.

Before sequencing, through artificially synthesis method of polymers of oligonucleotides, sequencing anchor should be synthesized into sequencing anchor with K numbers of degenerate bases is operable to hybridize to the DNA tags. Herein, K is a positive integer, generally within the range from 1 to 20. The idea is that the complementary strand of the portion of the adaptor sequences in DNA tags is used as general sequence of sequencing anchor. Then based on this general sequence, K numbers of degenerate bases are added to the end. In this invention, said sequencing anchor with K numbers of degenerate bases can be various sequences, such as extension primer, polymerase extension primer and etc. It should be stated that said extension primer is referred to sequencing anchor that is used by ligase in ligation reaction. Polymerase extension primer is referred to sequencing anchor that is used by DNA polymerase during sequencing reaction.

Step 231 is process of hybridization between sequencing anchor with K numbers of degenerate bases and DNA tags immobilized on vector's surface.

Step 232, sequencing anchor is extended along DNA tags through K numbers of degenerate bases. Sequencing signal is produced during extension process. Herein, degenerate polymers include multiple forms, such as hexamers, heptamers, octamers, nonamers and etc. Moreover, there are multiple ways for degenerate polymers labeling, including biotin labeling, fluorescence labeling and etc. There are multiple ways of fluorescence labeling including 4 color fluorescence labeling, 2 color labeling and etc. Take degenerate nonamers as example. Method of fluorescence labeling is as the following (1) if method of 4 color fluorescence labeling nonamers is taken, one set of fluorescent labeling can be used for 3' end and the other set can be used for 5'. Herein, ligation of degenerate polymers of oligonucleotides should be designed beforehand. Thus 6 to 7 bases can be called from the ligation site between extension primer and DNA tags. Then sequencing anchor with K numbers of degenerate (i.e. K=6) bases is used for further sequencing. In this exemplary embodiment, the length of extended primer is optimized. By using different extension primers with different numbers of degenerate bases, up to 12 bases can be sequenced from the same end. Therefore, this method of sequencing can be used to analyze complicated target sequences (e.g. human genome sequences). In order to further increase the strength of the output signal, in this invention, a 2 color detection method is in place of 4 color detection method. In 2 color detection method, strong fluorescence labeling can be used, such as Cy3, TAMRA, Texas Red, TEX613 or etc. In an exemplary experiment, by using ligation mixture of two fluorescence labeled degenerate polymers and two non-labeled degenerate polymers (e.g. Cy3-A, Texas Red-G, -T, -C), sequencing signal of DNA tags immobilized on glass slides or microbeads can be detected. Then extension primers and ligated degenerate polymers are removed. Mixture of the same extension primer and degenerate polymers different from the above (e.g. Cy3-T, Texas-Red-C, -A, -G) is used to do another sequencing. Sequencing signal can be produced. Detection of two ligation reaction can obtain a complete set of data information of all 4 bases.

In another exemplary embodiment, if sequencing anchor with K numbers of degenerate bases is polymerase extension primer, polymerase, nucleotide, labeled nucleotide (biotin label or fluorescence label) are added into polymerase extension primer mix. DNA polymerase extends the 3' end of extension primer along DNA tags. Sequencing signal is produced along extension process. After this step, DNA strand extended from extension primer by polymerase should be removed. Removal of DNA strand can vary, such as denature (low salt and high temperature), or exonuclease digestion (e.g. λexonuclease) or enzyme accompanied denature (e.g. when dUTP is used in extension mixture, enzyme could be Uracil-DNA glycosylase or DNA glycocylase, and endonuclease VIII).

In an optimized exemplary embodiment, in order to increase the sequencing accuracy, said Step 232 can adapt overlapping sequencing mechanism or type IIs restriction enzyme walking mechanism. Details are (1) in overlapping sequencing mechanisms, with sequencing anchor in both ends, DNA tags can be sequenced bi-directionally from both ends. Sequence can be called bi-directionally. (2) in type II restriction enzyme walking mechanism, by using type II restriction enzyme site in the first adaptor sequence of DNA tags, portion of sequenced DNA tags is cut off. New adaptor sequence is ligated to type II restriction enzyme site. Thus new DNA tags are constructed. Sequencing is continued by using new adaptor sequence. Sequencing results of the remaining region in said DNA tags can be obtained afterwards.

Figure 8:
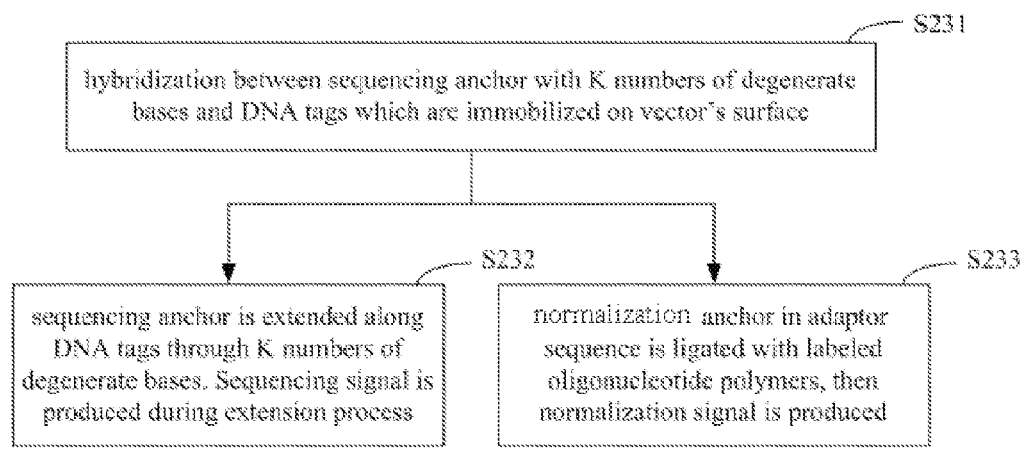
FIG. 8 is a flow chart showing method of sequencing DNA tags using sequencing anchor with at least one degenerate used in another exemplary embodiment of this invention.
Figure 9:
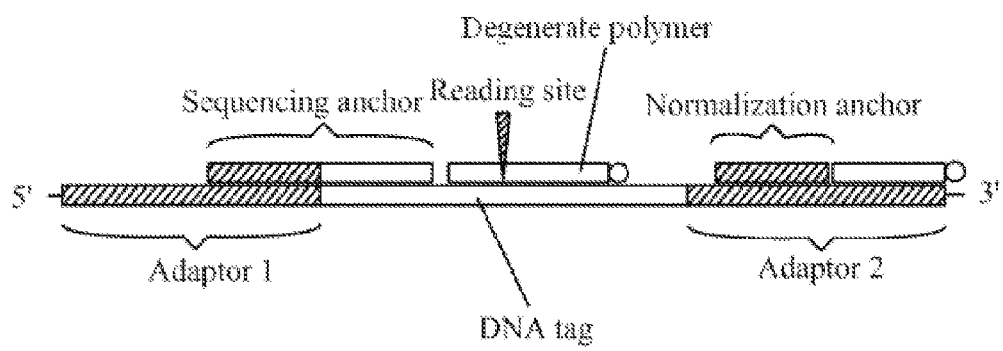
FIG. 9 is a schematic diagram showing sequence process using extended primer as sequencing anchor as used in another exemplary embodiment of this invention.

In another optimized exemplary embodiment, as shown in FIG. 8 and FIG. 9. if normalization anchor is included in the adaptor sequence of DNA tags, then when Step 232 is carried out, normalization anchor in adaptor sequence is ligated with labeled oligonucleotide polymers. Normalization signal is produce. Thus in following data processing, reaction efficiency of multiple cycles can be normalized. Thus difference between each reaction can be eliminated and the accuracy of sequencing can be raised.

Figure 10:
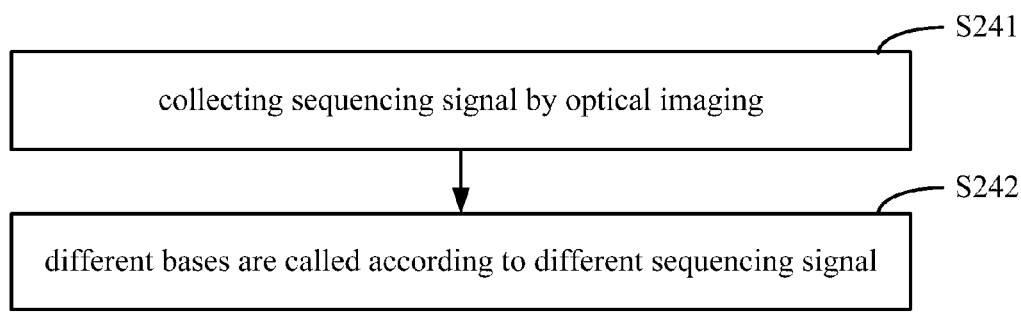
FIG. 10 is a flow chart illustrating method of collecting sequencing signal, data processing and calling sequences of DNA tags in an exemplary embodiment of this invention.

In an exemplary embodiment, FIG. 2 Step 24, the detailed process of sequencing signal collection, data processing and sequence of DNA tags calling is shown in FIG. 10, including following steps.

In an optimized exemplary embodiment, when said Step 232 is performed and normalization signal is produced, normalization signal is collected at the same time as Step 241 is conducted. Normalization signal is that used to normalize collected sequencing signal. Difference between different reactions is eliminated. In an exemplary embodiment of this invention, normalization is embodied by the ratio of sequencing signal versus normalization. For example, Signal No. 1 is X and signal No. 2 is Y and normalization signal is M. Sequencing signal after normalization is X/M and Y/M separately.

In Step 242, different bases are called according to different sequencing signal, i.e. said sequence of DNA tags. In this invention, according to discrete characteristics of base complementary, type of bases is determined in DNA tags.

Figure 11:
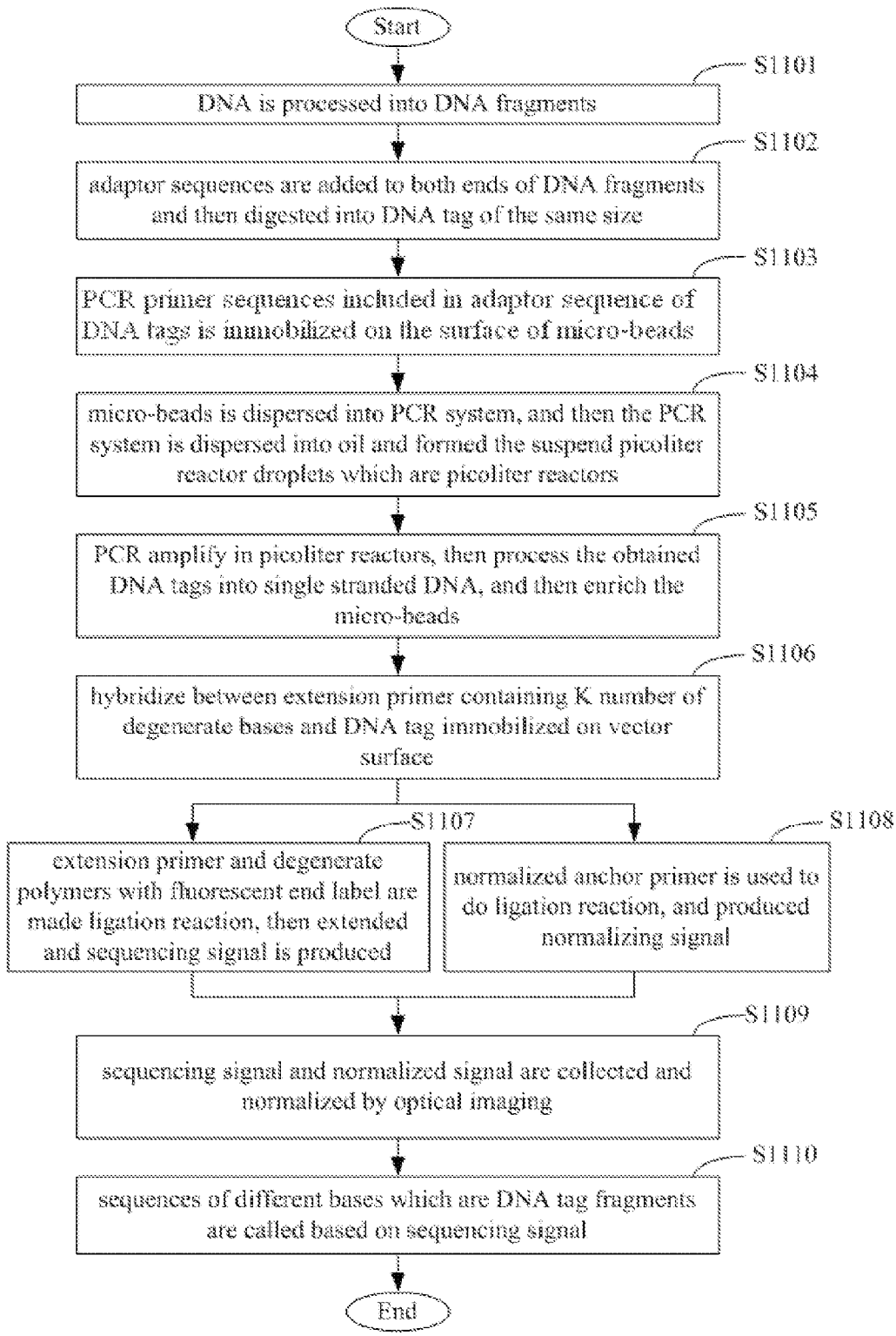
FIG. 11 is a flow chart illustrating DNA sequencing method in an optimized embodiment of this invention.

FIG. 11 is a flow chart illustrating DNA sequencing method in an optimized embodiment of this invention. This embodiment is an optimized embodiment, the application exemplary is extension primer to sequencing anchor primer, micro-beads to vector.

Step 1101, DNA is processed into DNA fragments.

Step 1102, Adaptor sequences are added to both ends of DNA fragments and then digested into DNA tags of equal size.

Step 1103, PCR primers included in adaptor sequence of DNA tags is immobilized on the surface of micro-beads.

Step 1104, Micro-beads is dispersed into PCR system, and then the PCR system is dispersed into oil and formed the suspend picoliter reactor droplets which are picoliter reactors.

Step 1105, PCR amplify in picoliter reactors, then process the obtained DNA tags into single stranded DNA, and then enrich the micro-beads.

Step 1106, Hybridize between extension primer containing K number of degenerate bases and DNA tag immobilized on vector surface.

Step 1107, extension primer and degenerate polymers with fluorescent end label are made ligation reaction, then extended and sequencing signal is produced.

Step 1108, Normalized anchor primer is used to do ligation reaction, and produced normalizing signal.

Step 1109, Sequencing signal and normalized signal are collected and normalized by optical imaging.

Step 1110, Sequences of different bases which are DNA tag fragments are called based on sequencing signal.

An exemplary embodiment of the above optimal selection in FIG. 11:

Hybridization between extension primer and DNA tag, that is the extension primers matching the sequencing anchor of the tag directly. Then the extension primer have ligation reaction with a set of degenerate nonamer labeled fluorescence (NNNNNNNNN) The degenerate nonamer is mixed by 4 kinds of nonamers. To read the sequence of the base, in some site, the types x of the base in the 4 kinds of nonamers, have the same type of the fluorescence-labeled. (eg NNNX-NNNNN, X=A, T, C, G) Because of the resolution characteristics of the ligase's base complementary in X site of the nonamer, the type of the base in the sequence of tag can be inferred. Because extended primer contains K number of degenerate bases (ie. K=1, 2, 3, 4, 5, 6), the sequence in DNA tag can be read by different number of degenerate base and the same set of nonamers (i.e. XNNNNNNNN, X=A, T, C, G). Or can use different set of extended primer and nonamer to read the base sequence located in the same site.

The most important characteristics of the methods used in this invention is that longer sequence of fragment can be called from DNA tags, for instance, 13 continuous bases. Current technology can only distinguish only within the sixth or seventh base of a fragment by ligase. In this invention positions beyond the tenth base from the point of extension primers on both ends can be called. By using the above methods, more than 20 bases of sequence can be called from 5' or 3' end to the binding point of sequencing anchor with DNA tags. Thus this method can be used for sequencing longer DNA tags generated by certain Type II restriction enzyme (such as MmeI, EcoP15I or etc.). Besides, designed indented primer series is also included in this invention. Indented primers are sequencing anchors shorter than the primer sequence of the tag sequence, for example, indenting to −3, −2, −1 position relative to the starting point of the unknown tag sequence. By using these indented primers, DNA tag sequence can be called using only one set of degenerate nonamers. For example, for NNNXNNNNN, if the fourth position is designed corresponding to 4 different AGCT in primers, then from the first to tenth base of DNA tags can be called.

Figure 12:
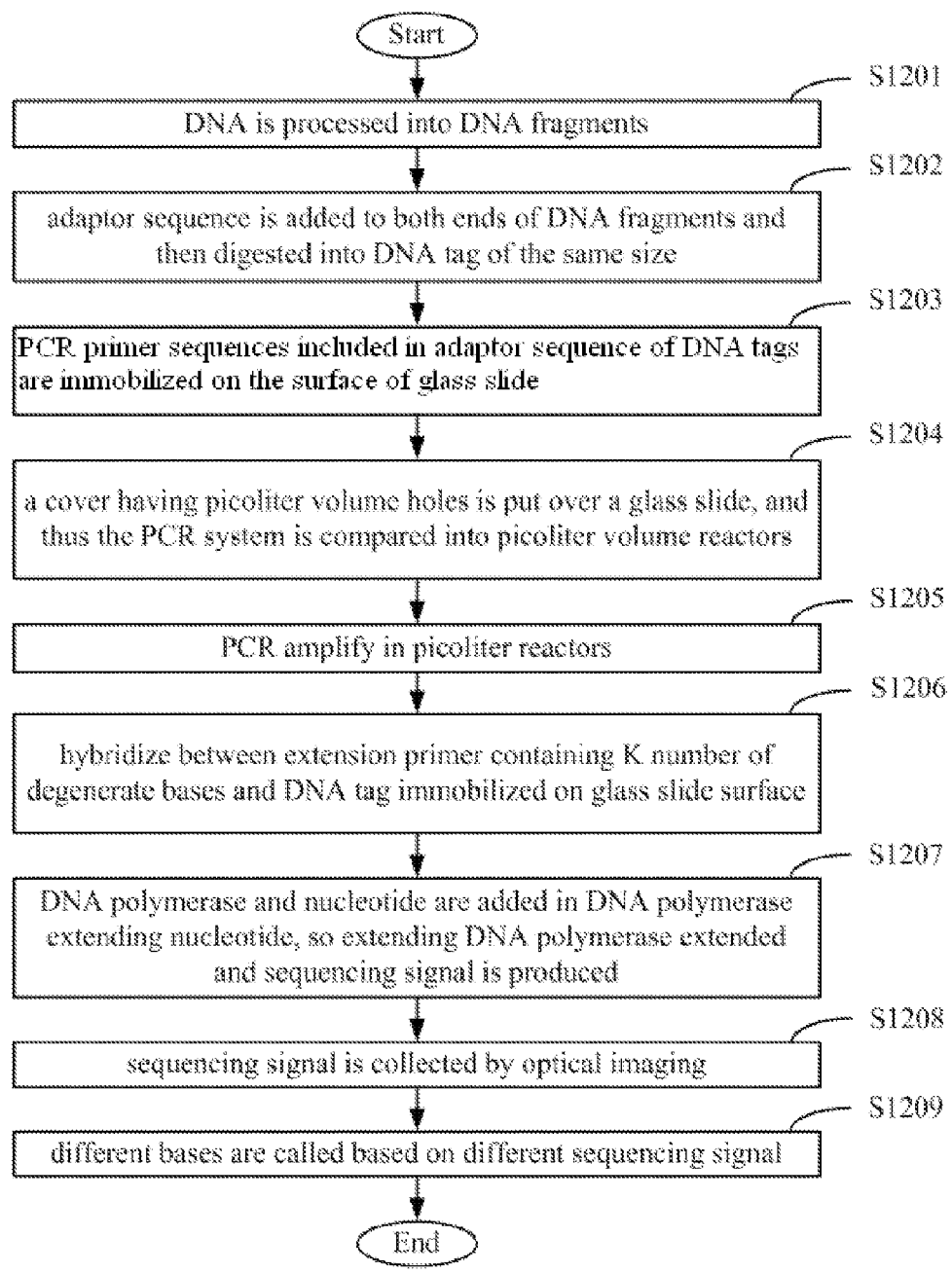
FIG. 12 is a flow chart illustrating DNA sequencing method in another optimized embodiment of this invention.

FIG. 12 is a flow chart illustrating DNA sequencing method in another optimized embodiment of this invention. This embodiment is another optimized embodiment, wherein polymerase extending primer to sequencing anchor primer and glass slide to vector. The details are in the following:

Step 1201, DNA is processed into DNA fragments.

Step 1202, adaptor sequence is added to both ends of DNA fragments and then digested into DNA tags of equal size.

Step 1203, PCR primers included in adaptor sequence of DNA tags are immobilized on the surface of glass slide.

Step 1204, A cover having picoliter volume holes is put over a glass slide, and thus the PCR system is compared into picoliter volume reactors.

Step 1205, PCR amplify in picoliter reactors.

Step 1206, Hybridize between extension primer containing K number of degenerate bases and DNA tag immobilized on glass slide surface.

Step 1207, DNA polymerase and nucleotide are added in DNA polymerase extending nucleotide, so extending DNA polymerase extended and sequencing signal is produced.

Step 1208, Sequencing signal is collected by optical imaging.

Step 1209, Different bases are called based on different sequencing signal.

Figure 13:
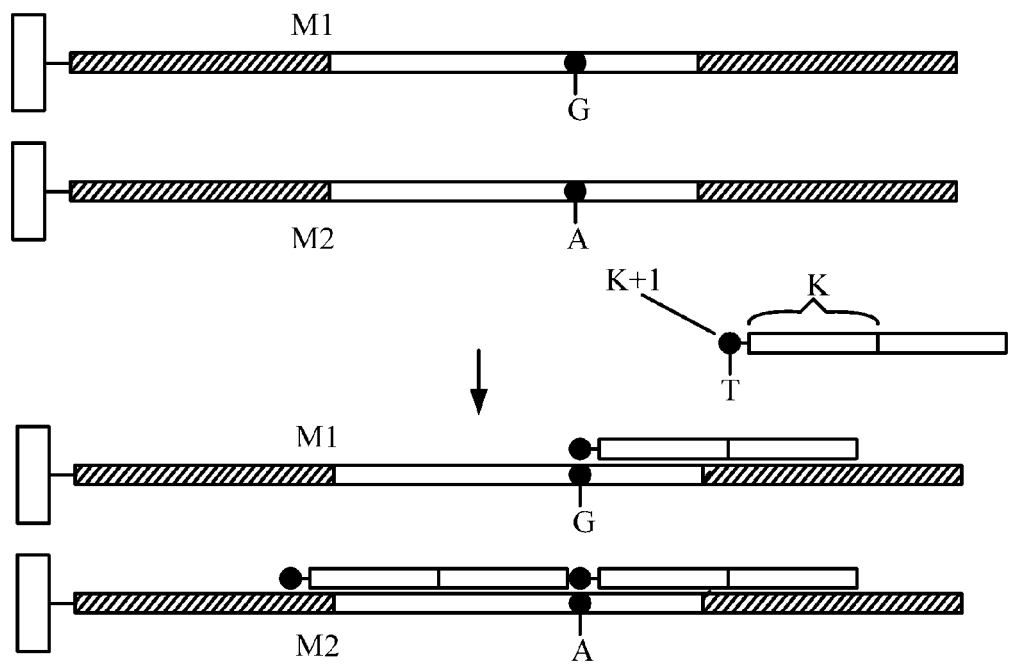
FIG. 13 is a schematic diagram showing sequencing process using PCR extensive primer as sequencing anchor in another optimized embodiment of this invention.

In one of the optimized embodiment shown in FIG. 12, process of sequencing using DNA polymerase extending primer to be sequencing primer will be shown in FIG. 13:

In this exemplary embodiments DNA polymerase extending primer includes the sequence complementary to anchor primer sequence in DNA tags, DNA polymerase extending primer also contains K number of different length degenerate bases and 3' end of DNA polymerase extending primer contains specific bases (A, T, G, C). DNA polymerase extending primer is used to hybridize with DNA tag immobilized on vector surface (micro-beads or glass slide).

When DNA polymerase added, the 3' end of primer hybridizing with DNA tag is extended. Because of selectivity of DNA polymerase, the primer containing complementary bases to DNA tag at 3' end can extended along tag template and produce signal. When mixing labeled nucleotide into extending mixture, DNA tag extended correctly can be recognized correctly. Otherwise the primer not containing complementary bases can not be extended, therefore will not produce signal.

According to the theory of base specification the anchor primer containing different base on its 3' end can be applied in this DNA tag, therefore deduce the sequence of different DNA tag based on different signal labeled on each DNA tag. The number of complementary bases (ie. K=1-9) may decide the information of the base located in K+1 position downstream anchor DNA tag. For example, the primer constructed as "anchor primer-NNN-A/T/G/C", can decide the base located in 4 base downstream the anchor primer, which means the 4th base.

This invention provides two exemplary embodiments. Details are as the following:

Example one is the scenario of sequencing by using extension primer. In this exemplary embodiment, DNA to be sequenced is processed DNA fragments with adaptor sequences on both ends and a normalization sequence.

Sequence of short DNA tags is 5'-CCACTACACTGG-TACT CCTCATCGATGACGTACGACT-CGATTAC-GAATCG-CTAGCATTCGGA CTCGATACGAAGTC-GATCGATGAGA-3' (SEQ ID NO: 1).

Among the sequence, 5'-CCTCATCGATGACGTAC-GACT-3' (SEQ ID NO: 2) is the adaptor portion of DNA tags. Its complementary strand (5'-AGTCGTACGTCATCGAT-GAGG-3') is the general sequence in sequencing anchor. Sequencing anchor is synthesized according to said general sequence with additional degenerate bases (e.g. K=1-9). For example, in 5'-AGTCGTACGTCATCGATGAGGN-3' (SEQ ID NO: 5), there is one degenerate base.

5'-CGATTACGAATCG-3' (SEQ ID NO: 6) is a DNA to be sequenced

5'-CGATACGAAGTCGATCGATG-3' (SEQ ID NO: 3) is normalization sequence in sequencing anchor.

For this DNA to be sequenced, the detailed experimental operation of sequencing is as the following:

(1) DNA is copied into multiple copies by single molecule PCR and immobilized on surface of micro-beads. After basic denature of DNA tags, single stranded DNA is obtained and immobilized on surface of micro-beads on its 5' end.

(2) By covalently amino linked, micro-beads are immobilized on the surface of glass loading film. Thus DNA tags to be sequenced are immobilized on the same level.

(3) Sequencing anchor (5'-AGTCGTACGTCATCGAT-GAGGN-3' (SEQ ID NO: 5)) and normalization anchor (5'-CATCGATCGACTTCGTATCG-3' (SEQ ID NO: 4)) are hybridized with single stranded DNA in hybridization buffer (such as SSC, SSPE or etc.). Temperature of the system is first raised (50-80° C.) and then followed by a graduate drop. Thus correct pairing between template and two anchors is obtained.

(4) After replacing reaction buffer with ligation buffer, ligase and fluorescent labeled oligonucleotide polymers and fluorescence labeled normalization polymers are all added in. Reaction temperature is controlled within the range between 20° C. to 30° C. Time of reaction is 1 minute to 30 minutes.

(5) Remains of non ligated reactant is washed off and is replaced by washing buffer.

(6) For fluorescent optical imaging of micro-beads, corresponding bases sequenced by anchor and oligonucleotide are recorded. Normalization signal is recorded as well.

(7) After buffer is replaced, enzyme mixture is added to remove extended DNA. Enzyme used can be for example uracil-DNA glycosylase (UDG) or mixture of UDG and endonuclease VIII. When the reaction temperature is raised to 30° C.-37° C. for 1 to 10 minutes, U position amid of sequencing anchor can be cut off.

(8) After buffer is replaced by denaturing buffer, when system temperature is raised to 45° C.-65° C., the short ligated DNA strand is removed and DNA is recovered into its original single stranded status.

(9) By choosing different anchor (anchor with different numbers of degenerate bases e.g. 5'-AGTCGTACGTCATC-GATGAGGNN-3' (SEQ ID NO:7) and 5'-AGTCGTACGT-CATCGATGAGGNNN-3'), and depending on the characteristics that different position correspond to different oligonucleotide polymers, sequencing information can be obtained from the same reaction steps involving bases at other positions in DNA tags. In this exemplary embodiment, the ultimate sequence called is 5'-CGATTACGAATCG-3' (SEQ ID NO: 6), same as the original sequence of DNA fragment to be sequenced.

Example two is the scenario of primer extension by polymerase. In this exemplary embodiment, DNA to be sequenced is processed DNA fragments with adaptor sequences on both ends and a normalization sequence.

Sequence of DNA tags is 5'-CCACTACACTGGTACT CCTCATCGATGACGTACGACT-CGATTACGAATCG-CTAGCATTCGGA CTCGATACGAAGTCGATCGAT-GAGA-3' (SEQ ID NO: 1).

Among the sequence, 5'-CTAGCATTCGGA-CTCGATA-3' (SEQ ID NO: 10) is the adaptor portion of DNA tags. Its complementary strand (5'-TATCGAGTCCGAATGCTAG-3' (SEQ ID NO: 8)) is the general sequence in sequencing anchor. Sequencing anchor is synthesized according to said general sequence with additional degenerate bases (e.g. K=1-9) and additional positioning base on 3' end. For example, as for the base at the third position of the sequence to be sequenced, a set of 4 sequencing anchors, composed of 5'-AGTCGTACGTCATCGATGAGGNN (A/T/C/G)-3' series are used to sequence any DNA sequence derivatives using 5'-CGATTACGAATCG-3' (SEQ ID NO: 6) as the portion to be sequenced.

For this DNA to be sequenced, the detailed experimental operation of sequencing is as the following:

(1) DNA is copied into multiple copies by single molecule PCR and immobilized on surface of micro-beads. After basic denature of DNA tags, single stranded DNA is obtained and immobilized on surface of micro-beads on its 5' end.

(2) By covalently amino linked, micro-beads are immobilized on the surface of glass loading film. Thus DNA tags to be sequenced are immobilized on the same level (3) Sequencing anchor (5'-TATCGAGTCCGAAT-GCTAGNG-3' (SEQ ID NO: 9)) is hybridized to sequencing template in hybridization buffer (such as SSC, SSPE or etc.). Temperature of the system is first raised (50-80° C.) and then followed by a graduate drop. Thus correct pairing between template and two anchors is obtained (4) After replacing reaction buffer with polymerase buffer, polymerase, fluorescence labeled nucleotide and regular nucleotide are all added in the reaction system. Reaction temperature is controlled within the range between 20° C. to 30° C. for 1 to 10 minutes.

(5) Remains not to react is washed off and is replaced by washing buffer (6) For fluorescent optical imaging of micro-beads, micro-beads with extension at the end are recorded. Since extension only occurs when the end of sequencing anchor is correctly paired with DNA fragment to be sequenced (in this example, G is on sequencing anchor and C is on the sequence to be tested), signal is recorded for the base in DNA fragment corresponding to the end of sequencing anchor. If sequencing anchors other than the correct one is chosen, base pairing can't be correct and extension won't happen. Thus base at the position to be sequenced can be correctly called.

(7) After buffer is replaced, enzyme mixture is added to remove extended DNA. Enzyme used can be for example uracil-DNA glycosylase (UDG) or mixture of UDG and endonuclease VIII. When the reaction temperature is raised to 30° C.-37° C. for 2 to 10 minutes, U position amid of sequencing anchor can be cut off.

(8) After buffer is replaced by denaturing buffer, when system temperature is raised to 45° C.-65° C., the newly synthesized DNA strand is removed and DNA is recovered into its original single stranded status.

(9) Similar method using sequencing anchor with ends of three other bases is adapted to sequence DNA fragment. After testing all 4 sequencing anchors corresponded to different bases, the correct base can be called in the template sequence corresponding to the base at the end of sequencing anchor.

(10) By choosing sequencing anchors with different numbers of degenerate bases (e.g. 5'-TATCGAGTCCGAAT-GCTAGNN(A/T/C/G)-3', 5'-TATCGAGTCCGAAT-GCTAGNNN (A/T/C/G)-3'), sequencing information can be obtained by using same reaction steps at different base positions at template. In this exemplary embodiment, the ultimate sequence to be called is 5'-CGATTACGAATCG-3' (SEQ ID NO: 61 same as the original sequence of DNA fragment to be sequenced.

Figure 14:
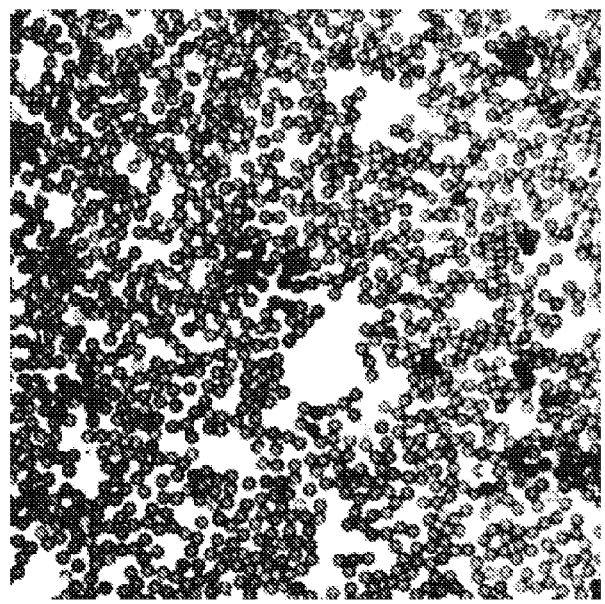
FIG. 14 is a schematic diagram showing imaging of sequencing in an exemplary embodiment of this invention. Base G is called by Cy3 labeled degenerate polymers in this test.

FIG. 14 is a diagram of images obtained in the above two exemplary embodiments. Base G is called by Cy3 labeled polymers in this test. Density of the sample is very high and signal to noise ratio is very high too. Experimental conditions are 10× objects, NA=0.3, 100 W mercury lamp, CCD 2 s exposure.

Figure 15:
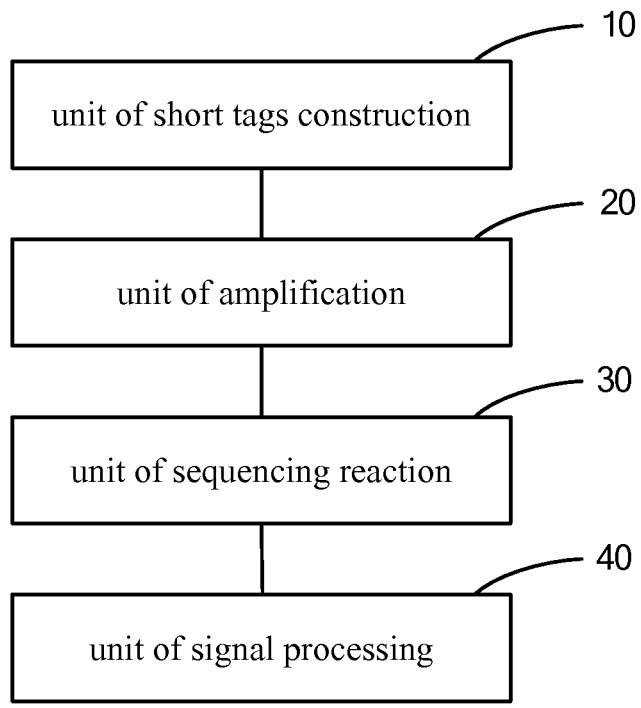
FIG. 15 is a system structure diagram of sequencing process used in an exemplary embodiment of this invention.

FIG. 15 shows system structure of DNA sequencer in an exemplary embodiment of this invention, including unit of short tags construction 10, unit of amplification 20, unit of sequencing reaction 30, unit of signal processing 40.

(1) Unit of short tags construction 10. Aiming to process DNA into multiple DNA segments, and then constructed into multiple DNA tags.

(2) Unit of amplification 20. Connected to unit of short tags construction 10, every single DNA tag is amplified.

(3) Unit of sequencing reaction 30. Connected to unit of amplification 20, by using sequencing anchor which is operable to hybridize to the DNA tags and contains at least one degenerate base, every single DNA tag is sequenced and sequencing signal can be produced.

In an exemplary embodiment, said unit of sequencing reaction 30 includes:

A. Reaction chamber. Vector is placed on one of its inner wall. Multiple DNA tags are immobilized on said vector's surface. Receiving sequencing reaction reagents, sequencing of said DNA tags can be conducted in reaction chamber, and producing sequencing signal.

B. Reagent entry and exit are separately placed at the ends of the other side of the inner reaction chamber wall. Both are provided channels separately for reaction reagent entering and for reaction reagent exiting. In this invention, reagents used in sequencing reaction includes ligase and fluorescence labeled oligonucleotide or polymerase and fluorescence labeled oligonucleotide (4) Unit of signal processing 40 connected to unit of sequencing reaction 20, aiming to obtain sequences of every single DNA fragment from sequencing signal.

Figure 16:
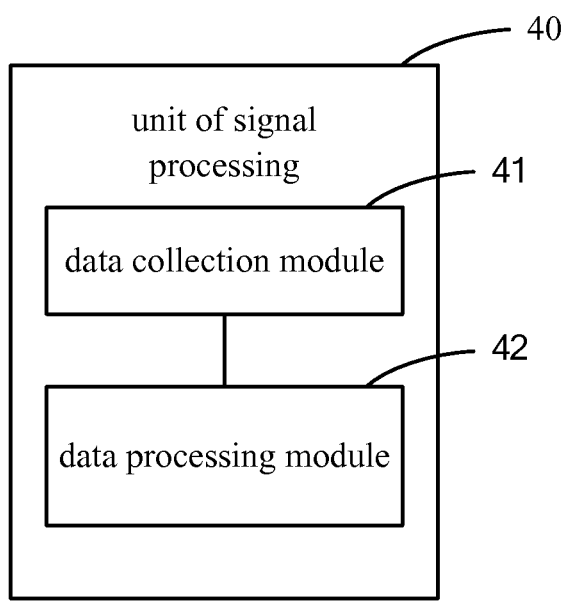
FIG. 16 is a structure diagram of signal processing unit used in an exemplary embodiment of this invention.

In an exemplary embodiment, as shown in FIG. 16, unit of signal processing 40 includes:

A. Data collection module 41, used for collecting said sequencing signal.

B. Data processing module 42, used for calling sequence of every single DNA fragment based on sequencing signal.

In an exemplary embodiment, data collection module 41 includes imaging components and reader. Imaging component can be large scale of CCD detector, for example, 4 to 11 million pixel CCD detectors. Thus high speed data collection can be embodied and throughput of all data can be raised.

All of the above is relative optimized embodiment in this invention, and is not to limit this invention. Any modification, equivalent replacement, optimization or etc. within the soul and principle of this invention is all included in the protection range of this invention.

What is claimed is:

1. A DNA sequencing method, which includes the following steps:

- A. Said DNA is processed into multiple DNA fragments, and then constructed into multiple DNA tags;
- B. Amplification of every single DNA tag, and then processed into single stranded DNA;
- C. Utilizing a sequencing anchor which is operable to hybridize to the DNA tags and contains at least one-degenerate base to sequence every single DNA tag and thus produce sequencing signal; and
- D. Obtaining sequences of every single DNA tag by sequencing signal, wherein step A includes:
  - A1. Ligating a first adaptor sequence to both ends of the DNA fragments;
  - A2. Cutting the ligated product with a restriction enzyme to generate a free 3' end and a free 5' end for each of the DNA fragments;
  - A3. Ligating a second adaptor sequence to the free 3' and 5' ends to produce DNA tags of equal size, the DNA tags each including the first adaptor sequence and the second adaptor sequence; said first adaptor sequence including a sequence complementary to the sequencing anchor, sequences of amplification primers, and a Type II restriction enzyme site used to process the DNA fragments into DNA tags of equal size; said amplification primers being configured for PCR; and said second adaptor sequence including an anchor sequence for normalization of sequence signals.

2. The DNA sequencing method according to claim 1, wherein prior to said step A1, process DNA into multiple DNA fragments, includes:

Fragmenting the DNA physically or cleaving the DNA by DNA enzyme.

3. The DNA sequencing method according to claim 1, wherein said step B includes:
- B1. Immobilizing PCR primer sequences included in adaptor sequence of DNA tags on vector's surface;
- B2. Compartmentalizing the product of step B1 into independent reactors, wherein each reactor includes an independent DNA tag;
- B3. Generating PCR in the said reactors and produce multiple copies of DNA tag; and
- B4. Processing the obtained DNA tags into single stranded DNA.

4. The DNA sequencing method according to claim 3, wherein said step B1 includes: immobilization of PCR primers on vector's surface through 5' covalent bonding or biotin binding.

5. The DNA sequencing method according to claim 4, wherein said vector in Step B1 includes glass slide or micro-beads.

6. The DNA sequencing method according to claim 5, wherein said reactors are picoliter reactors.

7. The DNA sequencing method according to claim 6, wherein said vector is defined by the glass slide, then the said Step B2 includes:
- Putting a cover made from soft silicon material and having picoliter volume holes over a glass slide, and thereby each picoliter volume hole defines a picoliter volume reactor wherein said picoliter reactors are said picoliter volume reactors.

8. The DNA sequencing method according to claim 6, wherein said vector is defined by the micro-beads, and said Step B2 includes:
- Dispersing the micro-beads into oil and forming the suspend picoliter reactor droplets, wherein said picoliter rectors are said picoliter reactor droplets.

9. The DNA sequencing method according to claim 8, wherein after said Step B3 a process for enrichment of the micro-beads is executed, the process for enrichment including:
- Immobilizing the micro-beads on a level surface by amino covalently linked and forming an enriched array.

10. The DNA sequencing method according to claim 1, wherein said Step C includes:
- C1: Hybridization between sequencing anchor containing K number of degenerate bases and DNA tag immobilized on a vector surface, K being a positive integer;
- C2: Extension along DNA tag by the K number of degenerate bases in the sequencing anchor to produce the sequence signal along the process.

11. The DNA sequencing method according to claim 10, wherein before said step C includes step C': artificially synthesizing said sequencing anchor.

12. The DNA sequencing method according to claim 11, wherein said step C2 includes following step:
- C2'. Utilizing the anchor sequence for normalization of the sequence signal in ligation reaction to promote the normalizing signal.

13. The DNA sequencing method according to claim 12, wherein said sequencing anchor with K number of degenerate bases includes an extension primer or a PCR extension primer.

14. The DNA sequencing method according to claim 13, wherein said sequencing anchor with K number of degenerate bases is the extension primer, step C2 includes ligation reaction between said extension primer and degenerate polymers with fluorescent end label, and then extension along the DNA tag, and producing sequencing signal along the extension.

15. The DNA sequencing method according to claim 14, wherein said degenerate polymers are respectively labeled by two or four kinds of fluorescent labels with different colors.

16. The DNA sequencing method according to claim 13, wherein said sequencing anchor with K number of degenerate bases is PCR extension primer, step C2 includes adding in DNA polymerase, nucleotide, labeled (biotin-labeled or fluorescence-labeled) nucleotide, extending along 3' end of DNA tag by polymerase, and producing sequencing signal along extension process.

17. The DNA sequencing method according to claim 16, wherein said sequencing anchor with K number of degenerate bases is PCR extension primer, step C2 further includes after step C2, removing DNA extended by polymerase along extension primer from the DNA tag immobilized on the vector's surface.

18. The DNA sequencing method according to claim 17, wherein the methods of said removing DNA extended by polymerase along extension primer includes: denature, or exonuclease digestion, or denature accompanied by digestion.

19. The DNA sequencing method according to claim 18, wherein said step D includes:
- D1. Collecting sequencing signal by optical imaging;
- D2. Calling different bases corresponding to different signals.

20. The DNA sequencing method according to claim 19, wherein said step D1 includes, collecting simultaneously sequencing signal and normalization signal by optical imaging.

21. The DNA sequencing method according to claim 10, wherein said step C2 further includes an overlapping sequencing mechanism, after the extension of DNA tag by the K number of degenerate bases in the sequencing anchor to produce the sequence signal along the process, the sequencing anchor is replaced with normalization anchor, which is complementary to the anchor sequence for normalization of sequence signal in second adaptor sequence, to repeat said extension step, then the sequence of every single DNA tag is bi-directionally sequenced from both ends of the DNA tag.

22. The DNA sequencing method according to claim 10, wherein said step C2 includes Type IIs restriction enzyme walking mechanism utilizing Type IIs restriction enzyme site in the first adaptor sequence of DNA tags, cutting off a portion of DNA that has been sequenced, and adding on a new adaptor sequence to the Type II restriction enzyme site and forming new and shortened DNA tags, and further sequencing from the new adaptor, and obtaining sequence results of the remaining regions in DNA tags.

* * * * *

```
                           SEQUENCE LISTING

<160> NUMBER OF SEQ ID NOS: 10

<210> SEQ ID NO 1
<211> LENGTH: 87
<212> TYPE: DNA
<213> ORGANISM: Artificial Sequence
<220> FEATURE:
<223> OTHER INFORMATION: Synthetic DNA

<400> SEQUENCE: 1
ccactacact ggtactcctc atcgatgacg tacgactcga ttacgaatcg ctagcattcg    60
gactcgatac gaagtcgatc gatgaga                                        87

<210> SEQ ID NO 2
<211> LENGTH: 21
<212> TYPE: DNA
<213> ORGANISM: Artificial Sequence
<220> FEATURE:
<223> OTHER INFORMATION: adaptor portion of DNA tags

<400> SEQUENCE: 2
cctcatcgat gacgtacgac t                                              21

<210> SEQ ID NO 3
<211> LENGTH: 20
<212> TYPE: DNA
<213> ORGANISM: Artificial Sequence
<220> FEATURE:
<223> OTHER INFORMATION: normalization sequence in sequencing anchor

<400> SEQUENCE: 3
cgatacgaag tcgatcgatg                                                20

<210> SEQ ID NO 4
<211> LENGTH: 20
<212> TYPE: DNA
<213> ORGANISM: Artificial Sequence
<220> FEATURE:
<223> OTHER INFORMATION: normalization anchor

<400> SEQUENCE: 4
catcgatcga cttcgtatcg                                                20

<210> SEQ ID NO 5
<211> LENGTH: 22
<212> TYPE: DNA
<213> ORGANISM: Artificial Sequence
<220> FEATURE:
<221> NAME/KEY: misc_feature
<222> LOCATION: (22)..(22)
<223> OTHER INFORMATION: Synthetic DNA, n is a, c, g, or t

<400> SEQUENCE: 5
agtcgtacgt catcgatgag gn                                             22

<210> SEQ ID NO 6
<211> LENGTH: 13
<212> TYPE: DNA
<213> ORGANISM: Artificial Sequence
```

```
<220> FEATURE:
<223> OTHER INFORMATION: Synthetic DNA

<400> SEQUENCE: 6
cgattacgaa tcg                                                          13

<210> SEQ ID NO 7
<211> LENGTH: 23
<212> TYPE: DNA
<213> ORGANISM: Artificial Sequence
<220> FEATURE:
<221> NAME/KEY: misc_feature
<222> LOCATION: (22)..(23)
<223> OTHER INFORMATION: Synthetic DNA, n is a, c, g, or t

<400> SEQUENCE: 7
agtcgtacgt catcgatgag gnn                                               23

<210> SEQ ID NO 8
<211> LENGTH: 19
<212> TYPE: DNA
<213> ORGANISM: Artificial Sequence
<220> FEATURE:
<223> OTHER INFORMATION: the general sequence in sequencing anchor

<400> SEQUENCE: 8
tatcgagtcc gaatgctag                                                    19

<210> SEQ ID NO 9
<211> LENGTH: 21
<212> TYPE: DNA
<213> ORGANISM: Artificial Sequence
<220> FEATURE:
<221> NAME/KEY: misc_feature
<222> LOCATION: (20)..(20)
<223> OTHER INFORMATION: Synthetic DNA, n is a, c, g, or t

<400> SEQUENCE: 9
tatcgagtcc gaatgctagn g                                                 21

<210> SEQ ID NO 10
<211> LENGTH: 19
<212> TYPE: DNA
<213> ORGANISM: Artificial Sequence
<220> FEATURE:
<223> OTHER INFORMATION: the adaptor portion of DNA tags

<400> SEQUENCE: 10
ctagcattcg gactcgata                                                    19
```